United States Patent [19] [11] 4,218,470
Casagrande et al. [45] Aug. 19, 1980

[54] EPININE ESTERS AND PHARMACEUTICAL COMPOSITIONS THEREOF

[75] Inventors: Cesare Casagrande, Como; Giorgio Ferrari, Milan, both of Italy

[73] Assignee: Simes Societa Italiana Medicinali e Sintetici S.p.A., Milan, Italy

[21] Appl. No.: 820,007

[22] Filed: Jul. 28, 1977

[30] Foreign Application Priority Data

Aug. 5, 1976 [IT] Italy ............................. 26074 A/76

[51] Int. Cl.$^2$ .................... C07C 93/26; A61K 31/215
[52] U.S. Cl. ..................................... 424/311; 560/142
[58] Field of Search ........................ 560/142; 424/311

[56] References Cited

U.S. PATENT DOCUMENTS

| | | | |
|---|---|---|---|
| 2,400,038 | 5/1946 | Buck | 560/142 |
| 3,809,714 | 5/1974 | Hussain et al. | 560/142 |
| 3,868,461 | 2/1975 | Hussain et al. | 560/142 |
| 4,031,242 | 6/1977 | Jones et al. | 560/142 |

*Primary Examiner*—Jane S. Myers
*Attorney, Agent, or Firm*—Cushman, Darby & Cushman

[57] ABSTRACT

Novel cardiocirculatory analeptics are prepared, which are epinine esters as obtained by reacting epinine (N-methyldopamine) with branched-chain aliphatic carboxylic acids. Exemplary members are 3,4-di-O-butyrylepinine and 3,4-di-O-pivaloylepinine. These medicaments are effective also by the oral route of administration, contrary to the hitherto commonly used dopamine derivatives which are rapidly destroyed by metabolization when administered orally.

6 Claims, No Drawings

EPININE ESTERS AND PHARMACEUTICAL COMPOSITIONS THEREOF

In the group of the biogenic amines, dopamine plays a well defined role and displays a particular therapeutic effect which is a result of its capacity of stimulating both the alpha- and the beta-adrenergic receptors, as well as the dopaminergic receptors. This complex physiological action is such as to give rise to a pattern of haemodynamic actions which are particularly useful in the cardiovascular therapeutics in order favorably to modify such situations as arterial hypotension, cardiocirculatory failures and cardiogenic shock.

Dopamine, however, is not absorbed when administered orally and, on the other hand, it is metabolyzed extremely quickly, so that it cannot be used in the therapeutics but intravenously by continuous infusion.

Many a study has been directed to the search for substances which are capable of displaying pharmacological actions which are akin to those of dopamine, even by oral administration. Among these studies a special place is deserved by the synthesis of dopamine esters with various carboxylic acids, such studies having been made by the present inventors (C. Casagrande, G. Ferrari, Il Farmaco, Ed. Sci., 28, 143 (1973). The substances of this class, even though they have displayed certain interesting pharmacological actions, did not show, however, such effects as prospectively to afford an efficient therapeutic action when administered orally.

It has now been surprisingly found that a group of novel esters of epinine (N-methyldopamine) with branched-chain carboxylic acids has such features, differently from the compounds known heretofore, as to unfold an efficient therapeutic action, akin to that of dopamine, also when administered by the oral route, so that a useful employment of these compounds as cardiocirculatory analeptics can be forecast.

It has been found, in addition, that by intravenous or parentheral administration of individual unit dosages of such compounds, effects which are comparable to those obtainable with the continuous administration of dopamine by slow intravenous infusion can be achieved.

The esters according to the present invention have the following general formula:

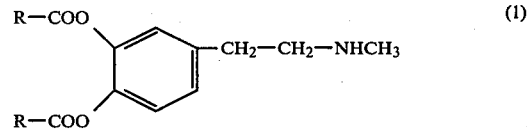

wherein R is a secondary or tertiary alkyl group having from 3 to 7 carbon atoms, and is preferably an isopropyl group or a tert. butyl group. This invention likewise contemplates the salts of the compounds referred to above with nontoxic inorganic or organic acids which are adapted to pharmaceutical use. The compounds of this invention are preferably administered orally in appropriate pharmaceutical presentations, such as tablets, fragees, geltin capsules, in combination with appropriate excipients or solvents for the soft-gelatine capsules. The compounds can also be formulated in solutions which are suitable for the oral administration, or also in solutions which are adapted to the parenteral or intravenous administration. The pharmaceutical formulations in the solid state for oral administration can be prepared with the appropriate expedients which are adapted to a delayed release of the active principle in order that a prolongation of the therapeutical effect may be achieved.

This invention has also as its object to provide two methods for synthesizing the esters of the formula (1) above, starting from epinine (2). Both methods have in common the fact of carrying out the acylation of both the phenolic hydoxyls without causing the acylation of the aminic moiety.

In the first procedure, as represented by the following pattern:

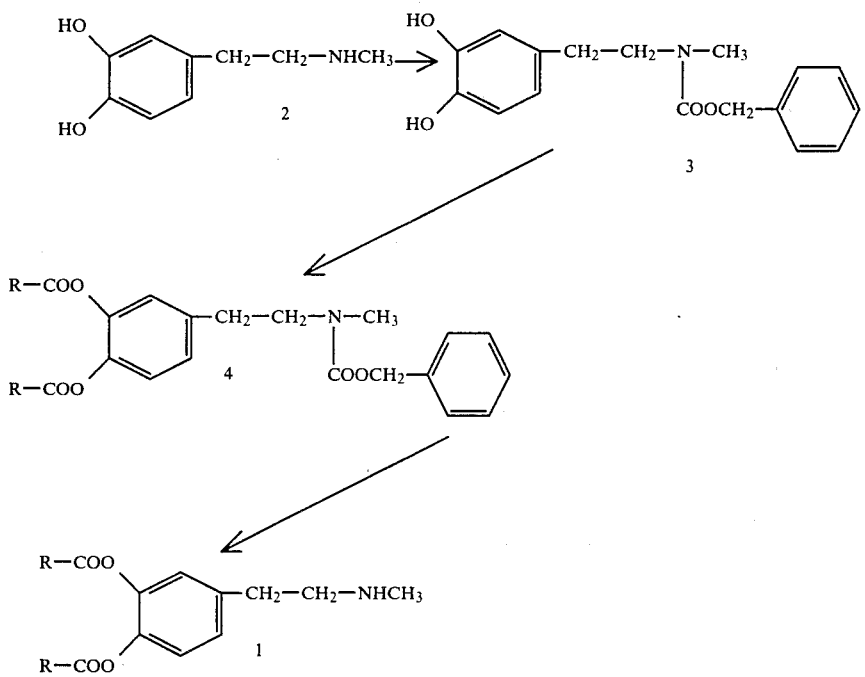

the aminic moiety is protected by the possible acylation by reaction with benzyl chlorocarbonate is an alkaline environment. The intermediate (3) which is obtained in this way is subsequently reacted with a reactive acyl derivative, such as anhydride, a chloride, a bromide, so as to obtain a compound of the formula (4). From the latter, by catalytic hydrogenation, an ester of formula (1) can be obtained.

In the second procedure, direct acylation of epinine is brought about by a reactive acyl derivative in an anhydrous environment and in the presence of a strong mineral acid, so that the aminic moiety is thoroughly protonated. Under such conditions, acylation involves the phenolic hydroxyls only and exclusively.

Preferred conditions for the first procedure are the reaction of epinine with benzyl in a molar ratio comprised between 1:1 and 1:2 chlorocarbonate in an aqueous solution which contains sodium hydroxide, and sodium tetraborate, in order to obtain the compound of the formula (3), followed by the reaction of the latter compound with an acyl chloride in pyridine solution, whereafter the catalytic hydrogenation in acetic acid is caused to occur, in the presence of a catalyst based on a metal of the platinum group, preferably palladium supported by charcoal.

Preferred conditions for the second procedure are the reaction of epinine with an acyl chloride in an inert solvent, preferably in an acylic or a cyclic ether, such as dioxan in the presence of anhydrous hydrogen chloride.

EXAMPLE 1

To a solution of 260 grams of sodium tetraborate and 160 grams of epinine hydrobromide in 1,750 mls of water, there is added, under a nitrogen blanket, 2-normal sodium hydroxide is added until attaining a pH of 9. With stirring, there are added during four hours, at 15° C., 165 grams of benzyl chlorocarbonate. Simultaneously, the mixture is supplemented with a quantity of 2-normal sodium hydroxide which is sufficient to keep the pH at the value of 9. Stirring is continued during 2 hours, the mixture is acidified and extracted with ethyl ether. The combined extracts are dried over anhydrous sodium sulfate and evaporated. N-carbobenzoxyepinine (formula 3) is thus obtained, which, recrystallized from isopropyl ether, has a melting point of 53° C.-54° C. To a solution of 30 grams of N-carbobenzoxyepinine (formula 3) in 200 mls of pyridine, are added, at 10° C., 27 mls of isobutyryl chloride. After allowing to stand for two hours at room temperature, the mixture is heated to 60° C. during 12 hours. On completion of this step, the mixture is diluted with ice and sodium bicarbonate solution, stirring is continued at room temperature for 30 minutes and extraction with ether is carried out, the extract is washed with a solution of diluted hydrochloric acid, dried over anhydrous sodium sulfate and evaporated off. The residue, which is 3,4-di-O-isobutyryl-N-carbobenzoxyepinine (formula 4 with R=isopropyl) is taken up with 250 mls. of glacial acetic acid and hydrogenated during 5 hours with 5 atmospheres of hydrogen in the presence of 2.5 grams of palladium on charcoal (10% Pd).

On completion of this step, the mixture is evaporated and the residue is treated with succinic acid. Thus, the 3,4-di-O-isobutyrylepinine hydrogen succinate is obtained (formula 1 for R=isopropyl) having a melting point of 118° C.-120° C. (cryst.from ethyl acetate).

EXAMPLE 2

With the same procedure as in Example 1, but replacing isobutyryl chloride with an equivalent amount of pivaloyl chloride the 3,4-di-O-pivaloylepinine hydrogen succinate is obtained (formula 2 for R=tert. butyl) having a melting point of 128° C.-130° C. (cryst.from ethyl acetate).

EXAMPLE 3

To a slurry of 40 grams of epinine hydrobromide in 160 mls of a 20% solution of anhydrous hydrogen chloride in dioxan are added 60 mls of isobutyryl chloride. The mixture is heated with stirring to 70° C. during 12 hours, evaporated to dryness under reduced pressures and the residue is recrystallized from ethyl acetate. Thus, 3,4-di-O-isobutyrylepinine hydrobromide is obtained (formula 1 for R=isopropyl) having a melting point of 124° C.-126° C.

By treating this hydrobromide with a solution of sodium bicarbonate, extracting with chloroform, evaporating the chloroform extract and treating the residue with succinic acid, the corresponding hydrogen succinate is obtained (melting point 118° C.-120° C.).

EXAMPLE 4

With the same procedure of Example 3 but replacing the isobutyryl chloride with an equivalent quantity of pivaloyl chloride one obtains the 3,4-di-O-pivaloyl-epinine hydrogen succinate (formula 1 for R=tert. butyl) having a melting point of 128° C.-130° C. (cryst. from ethyl acetate).

The compounds of the present invention have shown a slight toxicity when administered by the oral route. As a matter of fact, in mice, the compound (1) when administered orally, do not originate fatal casualties in the animals up to a dosage of 2 grams per kg b.w. The compound (2) in its turn, up to a dosage of 2 grams per kg b.w. orally, did not cause fatal casualties in animals. In order to ascertain the pharmacological properties of the compounds of the present invention, the compound (1) (that is, the 3,4-di-O-isobutyryl epinine) and the compound (2) (that is, the 3,4-di-O-pivaloyl epinine), have been tested in rats in comparison with (a) a non-branched ester of epinine, to wit 3,4-di-O-acetyl epinine (compd.3), (b) a branched ester of dopamine, to wit 3,4-di-O-isobutyryl dopamine (compound 4), and (c) a branched ester of the homolog, that is, of the N-ethyl dopamine. All the compounds have been administered in the form of an aqueous solution of their acid succinates at the dosage of 10 mg per kg. b.w. to rats which had been anesthesized with Nembutal.

An electromagnetic flowmeter has been located around the ascending aorta and a cannile has been inserted in the aorta lumen through the carotid artery. The maximum effect on the mean blood pressure, on the mean aortic flow and on the heart work (calculated in terms of the product of the mean arterial pressure) has been tabulated in Table 1 below, in the form of a percentage increase over the basal values, along with the duration of the action, i.e. the time required, after the administration, to return to the basal values.

TABLE 1

| Compound | Mean arterial pressure | Mean aortic flow | Cardiac work | Return to basal values, min. |
|---|---|---|---|---|
| 1 | +25 | +17 | +46 | 45 |
| 2 | +20 | +17 | +40 | 55 |
| 3 | +25 | +15 | +43 | 25 |
| 4 | +15 | +10 | +26 | 30 |
| 5 | — | +9 | +9 | 25 |

Both the compounds 1 and 2 have proven to be more active than the ester of dopamine (compound 4) and than the ester of N-ethyl-dopamine (compound 5).

The acetyl ester of epinine (compound 3) has proven to be active as the compounds 1 and 2, but its effect has a duration of 25 minutes only. On the other hand, epinine and dopamine are not absorbed and at 10 milligrams per kg b.w. they display no effect as a result of gastric administration.

The compounds of the present invention have exhibited pharmacological actions which are potentially advantageous as a result of oral administration to dogs, at dosages ranging from 1 to 10 milligrams per kg b.w., by increasing the contractive force of the heart while concurrently increasing the blood flow through the kidneys. At dosages comprised between 5 and 10 milligrams per kg b.w. also the mean arterial pressure rose. It can also be observed that the improvement of the heart contractility has been achieved without any increase of the heart rhythm: such as advantageous property is not exhibited by dopamine, which, as a result of intravenous administration, causes simultaneous and proportional increases both of the contractility and the heart rhythm.

The favourable effects of the compounds of the invention on the renal perfusion have been evidenced by the increase of the urinary secretion in rats as a result of oral administration.

We claim:

1. Esters of epinine with branched-chain carboxylic acids, having the following general formula:

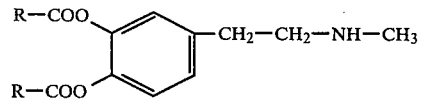

wherein R is a secondary or tertiary alkyl radical having from 3 to 7 carbon atoms, and their salts with non-toxic organic and inorganic acids.

2. An ester according to claim 1, characterized in that it is 3,4-di-O-isobutyrylepinine, having the formula (1) for R=isopropyl.

3. An ester according to claim 1, characterized in that it is 3,4-di-O-pivaloylepinine having the formula (1) for R=tert.butyl.

4. A pharmaceutical composition containing as the active ingredient a compound of claim 1 or a pharmaceutically acceptable salt thereof together with a galenic material, the active ingredient being present in an amount sufficient to provide a cardiocirculatory analeptic effect.

5. A composition according to claim 4 wherein the active ingredient is 3,4-O-isobutyrylepinine or a pharmaceutically acceptable salt thereof.

6. A composition according to claim 4 wherein the active ingredient is 3,4-di-O-pivaloylepinine or a pharmaceutically acceptable salt thereof.

* * * * *